United States Patent
Victor (10) Patent No.: US 10,325,471 B1
(45) Date of Patent: Jun. 18, 2019

(54) SYSTEMS AND METHODS FOR DETECTING A MEDICAL EMERGENCY EVENT

(71) Applicant: BLUEOWL, LLC, San Francisco, CA (US)

(72) Inventor: Jason Victor, San Francisco, CA (US)

(73) Assignee: BLUEOWL, LLC, San Francisco, CA (US)

( * ) Notice: Subject to any disclaimer, the term of this patent is extended or adjusted under 35 U.S.C. 154(b) by 0 days.

(21) Appl. No.: 15/961,320

(22) Filed: Apr. 24, 2018

Related U.S. Application Data

(60) Provisional application No. 62/491,447, filed on Apr. 28, 2017.

(51) Int. Cl.
*G08B 21/04* (2006.01)
*H04W 4/90* (2018.01)

(52) U.S. Cl.
CPC ............ *G08B 21/043* (2013.01); *H04W 4/90* (2018.02)

(58) Field of Classification Search
CPC ..... G08B 21/043; G08B 25/016; H04W 4/90; A61B 5/1116; A61B 5/1117; A61B 5/6801; A61B 2562/0219
See application file for complete search history.

(56) References Cited

U.S. PATENT DOCUMENTS

| | | | |
|---|---|---|---|
| 2011/0181422 A1* | 7/2011 | Tran | G06F 19/3418 340/573.1 |
| 2011/0246123 A1* | 10/2011 | DelloStritto | A61B 5/11 702/141 |
| 2016/0171864 A1* | 6/2016 | Ciaramelletti | A42B 3/046 340/539.12 |

* cited by examiner

*Primary Examiner* — Orlando Bousono
(74) *Attorney, Agent, or Firm* — Hovey Williams LLP (57) ABSTRACT

A computer-implemented method for detecting medical emergency events may include, via one or more processors, data sensors, and/or transceivers: (1) obtaining sensor data indicative of kinetic actions of a user; (2) analyzing the sensor data to associate the sensor data with a one or more kinetic actions of the user; (3) comparing the one or more kinetic actions of the user with a model of kinetic actions to determine whether the one or more kinetic actions correspond with the model of kinetic actions, with the model being indicative of a medical emergency event; and (4) upon determining that the one or more kinetic actions correspond with the model, contacting medical emergency responders to request medical emergency services for the user. As such, medical emergency events being experienced by a user can be detected, and medical emergency responders may be quickly contacted to provide essential emergency medical services to the individual.

18 Claims, 4 Drawing Sheets

SYSTEMS AND METHODS FOR DETECTING A MEDICAL EMERGENCY EVENT

CROSS-REFERENCE TO RELATED APPLICATIONS

The current patent application is a non-provisional patent application which claims priority benefit with regard to all common subject matter to U.S. Provisional Application Ser. No. 62/491,447, titled "MEDICAL EMERGENCY EVENT DETECTION WITH AUTOMATED EMERGENCY RESPONSE", filed Apr. 28, 2017. The listed earlier-filed provisional application is hereby incorporated by reference in its entirety into the current patent application.

FIELD OF THE INVENTION

The present disclosure generally relates to computer-implemented methods, systems, and electronic devices for collecting data related to kinetic actions of an individual and for determining the existence of a medical emergency event based upon such kinetic actions.

BACKGROUND

Individuals who experience medical emergency events may require immediate medical services and/or treatment but may be incapacitated and unable to request for such services. For example, an individual that experiences a cardiac event (e.g., a heart attack) may become unconscious and collapse to the ground. Unless emergency medical responders are notified within minutes of the onset of the medical emergency event, the individual may have a low expectancy of surviving. Unfortunately, if the individual is alone, it is doubtful that emergency medical responders will be notified in sufficient time because the individual will likely be unconscious and/or otherwise incapacitated. Technology for determining the existence of a medical emergency event is presently lacking outside of expensive medical equipment, which is primarily used in hospitals or other medical facilities. Similarly, technology is also presently lacking for contacting emergency medical responders upon a determination being made that an individual is experiencing a medical emergency event.

BRIEF SUMMARY

Embodiments of the present technology relate to computer-implemented methods, systems, and electronic devices for collecting data related to kinetic actions of an individual and for determining the existence of a medical emergency event based upon such kinetic actions.

In a first aspect, a computer-implemented method for detecting medical emergency events may be provided. The method may include, via one or more processors, data sensors, and/or transceivers: (1) obtaining sensor data indicative of kinetic actions of a user; (2) analyzing the sensor data to associate the sensor data with a one or more kinetic actions of the user; (3) comparing the one or more kinetic actions of the user with a model of kinetic actions to determine whether the one or more kinetic actions correspond with the model of kinetic actions, with the model of kinetic actions being indicative of a medical emergency event; and/or (4) upon determining that the one or more kinetic actions correspond with the model of kinetic actions, contacting medical emergency responders to request medical emergency services for the user (such as via wireless communication or data transmission over one or more radio frequency links or digital communication channels). The method may include additional, fewer, or alternative actions, including those discussed elsewhere herein, and may be implemented via one or more local or remote processors, and/or via computer-executable instructions stored on non-transitory computer-readable media or medium.

In another aspect, a computer-implemented method for detecting medical emergency events may be provided. The method may include, via one or more processors, data sensors, and/or transceivers: (1) obtaining sensor data indicative of kinetic actions of a user; (2) analyzing the sensor data to associate the sensor data with one or more kinetic actions of the user; (3) comparing the one or more kinetic actions of the user with a sequential-action model of kinetic actions to determine whether the one or more kinetic actions correspond with the sequential-action model, with the sequential-action model being indicative of a medical emergency event; and/or (4) upon determining that the one or more kinetic actions correspond with the sequential-action model, contacting medical emergency responders to request medical emergency services for the user. The method may include additional, fewer, or alternative actions, including those discussed elsewhere herein, and may be implemented via one or more local or remote processors, and/or via computer-executable instructions stored on non-transitory computer-readable media or medium.

In another aspect, a computer-implemented method for detecting medical emergency events may be provided. The method may include, via one or more processors, data sensors, and/or transceivers: (1) obtaining sensor data indicative of kinetic actions of a user; (2) analyzing the sensor data to associate the sensor data with a kinetic action of the user; (3) comparing the kinetic action of the user with a single-action model of kinetic actions to determine whether the kinetic action corresponds with the single-action model, with the single-action model being indicative of a medical emergency event; and/or (4) upon determining that the kinetic action corresponds with the single-action model, contacting medical emergency responders to request medical emergency services for the user. The method may include additional, fewer, or alternative actions, including those discussed elsewhere herein, and may be implemented via one or more local or remote processors, and/or via computer-executable instructions stored on non-transitory computer-readable media or medium.

In another aspect, a mobile electronic device for detecting medical emergency events may be provided. The mobile electronic device may include one or more processing elements, transceivers, data sensors, and/or memory elements. The memory elements may include a program configured to instruct the processing elements to: (1) obtain sensor data indicative of one or more kinetic actions of the user; (2) analyze the sensor data to associate the sensor data with one or more kinetic actions of the user; (3) compare the kinetic actions of the user with a model of kinetic actions to determine whether the kinetic actions corresponds with the model of kinetic actions, with the model being indicative of a medical emergency event; and/or (4) upon determining that the kinetic actions correspond with the model of kinetic actions, contact medical emergency responders to request medical emergency services for the user. The mobile electronic device may include additional, fewer, or alternate components and/or functionality, including that discussed elsewhere herein.

In yet another aspect, non-transitory computer-readable medium with a program stored thereon for detecting medical emergency events may be provided. The program may instruct a processing element to perform the following: (1) obtain sensor data indicative of kinetic actions of a user; (2) analyze the sensor data to associate the sensor data with a one or more kinetic actions of the user; (3) compare the one or more kinetic actions of the user with a model of kinetic actions to determine whether the one or more kinetic actions correspond with the model of kinetic actions, with the model being indicative of a medical emergency event; and/or (4) upon determining that the one or more kinetic actions correspond with the model of kinetic actions, contact medical emergency responders to request medical emergency services for the user. The program stored on the computer-readable medium may instruct the processing element to perform additional, fewer, or alternative actions, including those discussed elsewhere herein.

Advantages of these and other embodiments will become more apparent to those skilled in the art from the following description of the exemplary embodiments which have been shown and described by way of illustration. As will be realized, the present embodiments described herein may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of computer-implemented methods, systems comprising computer-readable media, and electronic devices disclosed therein. It should be understood that each Figure depicts an embodiment of a particular aspect of the disclosed methods, media, and devices, and that each of the Figures is intended to accord with a possible embodiment thereof. Further, wherever possible, the following description refers to the reference numerals included in the following Figures, in which features depicted in multiple Figures are designated with consistent reference numerals. The present embodiments are not limited to the precise arrangements and instrumentalities shown in the Figures.

The Figures depict exemplary embodiments for purposes of illustration only. One skilled in the art will readily recognize from the following discussion that alternative embodiments of the systems and methods illustrated herein may be employed without departing from the principles of the invention described herein.

DETAILED DESCRIPTION

The present embodiments may relate to, inter alia, computing devices, software applications, systems, and methods for collecting data related to kinetic actions of individuals and for determining, based upon such kinetic actions, whether the individuals are experiencing medical emergency events. Embodiments of the computing device and/or system, through hardware operation, execution of the software application and/or computer program, implementation of the method, or combinations thereof, may be utilized as follows. The computing device of an individual, such as in the form of a mobile electronic device, may collect sensor data from one or more data sensors of the mobile electronic device. Such data may be indicative of kinetic actions made and/or experienced by the individual. Based upon such kinetic actions, embodiments may determine that the individual is experiencing a medical emergency event. In such case, embodiments may automatically contact emergency medical responders to request emergency medical services for the individual, even if the individual is unable to independently make such a request.

Presently, an individual that experiences a medical emergency event may have no method of contacting medical emergency responders for purposes of receiving emergency medical services. As used herein, the term Medical Emergency Event ("ME Event") may be used to mean an acute illness or injury that poses an imminent risk to an individual's life or long-term health. Examples of such ME Events may include: myocardial infarction (i.e., heart attack), stroke, diabetic episode, drug overdose, anaphylactic shock, epileptic seizure, accident (e.g., a fall from significant height, a vehicle/machine accident, etc.), or the like. Often, such ME Events may cause the individual to lose consciousness or to otherwise be incapacitated. As such, the individual may be unable to contact emergency medical responders, e.g., emergency medical technicians, paramedics, nurses, doctors, etc. (collectively "EM Responders") to obtain necessary emergency medical services or treatment ("EM Services"). Given the severity of such ME Events, the individual may have no more than five to six minutes upon the onset of the ME Event to contact EM Responders before the individual dies or the individual's long-term health is significantly compromised.

Certain embodiments of the present invention provide for the detection of an ME Event experienced by an individual and, in response, for the contacting of EM Responders, such that the individual can obtain requisite EM Services in sufficient time to reduce the likelihood of death and/or permanent injury that may otherwise result from the ME Event. In more detail, embodiments of the present invention may be configured to collect, in real-time, sensor data from data sensors of an individual's mobile electronic device. As used herein, the term "sensor data" is used to mean the data representing position, orientation, direction, displacement, velocity, and/or acceleration of the individual's mobile electronic device. Such sensor data may be obtained by various types of data sensors commonly found in mobile electronic devices, such as accelerometers. Because the individual will generally carry or otherwise hold his/her mobile electronic device, such sensor data may also be representative of the position, orientation, direction, displacement, velocity, and/or acceleration of the individual's physical body.

For instance, the sensor data may be indicative of the orientation of the individual's body, e.g. indicative of the individual standing upright, sitting down, lying down, or the like. In addition, the sensor data may be indicative of the direction, heading, and/or velocity at which the individual is travelling. Similarly, the sensor data may be indicative of the acceleration the individual is experiencing. Embodiments provide for such sensor data to be continuously collected in real-time. To ensure that such sensor data can be continuously collected, embodiments may include the use of a mobile electronic device that is commonly carried or worn by an individual, such as a smartphone, a smartwatch, smart glasses, wearables, smart clothes, or other handheld or wearable computing device.

Upon collecting such sensor data, embodiments of the present invention provide for an analysis of the sensor data so as to determine or detect kinetic actions of the individual. As used herein, the term kinetic actions may be used to mean physical body movements (or lack thereof), motions, or activities performed by or acted upon the individual. Examples of such kinetic actions include: (i) the individual's physical body being oriented in a particular manner (e.g., standing upright, leaning, sitting down, lying down, etc.), (ii) a change in the individual's orientation, (iii) the individual being immobilized (i.e., remaining generally motionless), (iii) the individual moving at a particular speed, (v) the individual falling or collapsing (or, more generally, moving under a particular acceleration), (vi) the individual making an impact, such as against an object or the ground, (vii) the individual convulsing (e.g., shaking or trembling), and/or the like. Based upon the kinetic actions, embodiments of the present invention are configured to determine or detect whether the individual is experiencing an ME Event.

In some embodiments, the existence of an ME Event may be determined by comparing an individual's kinetic actions with one or more ME Event models ("Event Model"). Event Models may be comprised of predetermined patterns or arrangements of kinetic actions, with such patterns or arrangements being indicative of ME Events. In some embodiments, the Event Models may include Sequential-Action Models. A Sequential-Action Model is an Event Model represented by a sequential pattern of kinetic actions. For example, in one embodiment, a Sequential-Action Model indicative of an ME Event may include the following kinetic actions in sequential order: an individual falling, the individual making an impact (e.g., with the ground), the individual remaining generally motionless. As such, if an individual experiences such a sequence of kinetic actions, embodiments may determine, based upon a comparison between the individual's kinetic actions with the Sequential-Action Model, that the individual has experienced an ME Event.

The following is a specific example of detecting an ME Event, in the form of a heart attack, as such an event is experienced by an individual. The individual may initially be oriented in a standing, upright position. Such an orientation may be detected by the data sensors of the individual's mobile electronic device. From the standing position, the individual may fall or collapse to the ground. The kinetic action of falling may be determined based upon sensor data obtained by the accelerometer of the individual's mobile electronic device. Specifically, the accelerometer may sense the acceleration of the individual as the individual falls to the ground. In some embodiments, such an acceleration may have a magnitude that corresponds with the earth's gravitational acceleration.

In addition to the acceleration, one or more of the sensors of the individual's mobile electronic device may sense a change in the individual's orientation during the fall (e.g., a transition from an upright position to a horizontal position, e.g., prone, supine, or the like). Given the detection of the acceleration and/or the change in the individual's orientation, embodiments of the present invention may determine that the individual has experienced a kinetic action in the form of falling. The kinetic action of falling may, in some embodiments, correspond with an initial kinetic action that is part of a Sequential-Action Model indicative of a heart attack-type ME Event.

Continuing with the above heart attack scenario, the kinetic action of falling may be followed by the individual making an impact, and in particular, making an impact with the ground. The accelerometer of the individual's mobile electronic device may sense the quick deceleration of the individual's body during such an impact. In some specific embodiments, upon the individual impacting the ground, the individual's body may experience a small bounce before coming to rest on the ground. The accelerometer of the individual's mobile electronic device may detect the bounce as a number of short, alternating changes in the acceleration (i.e., direction and/or magnitude) experienced by the individual. Given the detection of the deceleration and/or the bounce, embodiments of the present invention may determine that the individual experienced a kinetic action in the form of an impact with the ground. The kinetic action of the impact may, in some embodiments, correspond with an intermediate kinetic action that is part of the Sequential-Action Model indicative of a heart attack-type ME Event.

Finally, after the individual impacts the ground, the individual experiencing the heart attack may experience the kinetic action of remaining generally motionless for a period of time. Such a motionless state may correspond to the individual being unconscious, and may be sensed by one or more of the data sensors of the individual's mobile electronic device, such as the accelerometer. The kinetic action of being motionless for a period of time may, in some embodiments, correspond with a final kinetic action that is part of the Sequential-Action Model indicative of a heart attack-type ME Event.

Given the sequential pattern of kinetic actions described above, embodiments of the present invention may determine that the individual has experienced an ME Event, in the form of a heart attack. In particular, an analysis of the sensor data collected by the sensors of the mobile electronic device may indicate the individual underwent each of the above-described kinetic actions (i.e., falling, impacting the ground, and remaining motionless). Embodiments of the present invention may further analyze such kinetic actions by comparing them with one or more Event Models, including the Sequential-Action Model indicative of a heart attack-type ME Event. Upon determining that the kinetic actions experienced by the individual correspond with, or match, the Sequential-Action Model indicative of a heart attack attack-type ME Event, embodiments may determine that the individual was likely to have experienced a heart attack-type ME Event. Specifically, as described above, the Sequential-Action Model of a heart attack-type ME Event may include the following kinetic actions, in sequential order: (i) a fall, (ii) an impact, and (iii) a motionless period. As such, when the data sensors of the individual's mobile electronic device sense sensor data indicative of kinetic actions that correspond, in order, with (i) the individual falling, (ii) the individual impacting the ground, and (iii) the individual remaining motionless for a period of time, embodiments of the present invention may determine that the individual has experienced an ME Event, such as a heart attack.

In response to a determination that the individual has experienced an ME Event, embodiments pay provide for EM Responders to be contacted so that the individual can receive EM Services. In particular, the individual's mobile electronic device may display an alert message on a display of the mobile electronic device. The alert message may be in the form of a health status question, requesting whether the individual is in need of EM Services. The mobile electronic device may accept inputs from the individual in response to the health status question. For instance, the individual may provide an answer indicating that individual is not in need of EM Services, in which case no further actions may be taken. Alternatively, if the individual provides an answer indicating that the individual is need of EM Services, embodiments may provide for EM Responders to be contacted. In some embodiments, the mobile electronic device may contact EM Responders by way of a voice communicating connection over a cellular network. Alternatively, a text-based communication connection over a data network may be used. The individual may be able to communicate with the EM Responders over such networks, or, alternatively, an automated message (e.g., automated voice message, text message, email message, or the like), may be sent to the EM Responders over the networks.

However, it should be understood that the individual may only be able to provide an answer to the health status question if the individual is conscious and/or capable of manipulating a user input of the mobile electronic device. If the individual is unconscious or is otherwise unable to manipulate the user input of the mobile electronic device, embodiments of the present invention may, nevertheless, provide for EM Responders to be automatically contacted, even if the individual does not provide any response to the health status question. Specifically, for instance, if the individual does not provide an answer to the health status question within a predetermined time period, such as within 5 seconds, 10 seconds, 15 seconds, 20 seconds, or more, embodiments may automatically contact EM Responders to request EM Services for the individual. Such contact may be via an automated voice message, a text message, an email message, or the like. In addition to requesting EM Services, the mobile electronic device may provide location information for the individual, such as may be based upon location determining element (as described in more detail below) within the mobile electronic device.

The above-described introduction provides an introduction to embodiments of the present invention, which include computer-implemented methods, systems, and electronic devices for collecting sensor data indicative of kinetic actions of an individual, and for determining the likelihood of the individual experiencing an ME Event based upon such kinetic actions. Upon determining that an individual has likely experienced an ME Event, embodiments may provide for EM Responders to be contacted so as to provide EM Services to the individual. The contacting of EM Responders may be performed automatically, such that even if the individual has experienced an ME Event that renders the individual unconscious or otherwise incapacitated, EM Responders can be still be contacted to provide EM Services to the individual.

Exemplary Embodiments for Collecting Sensor Data and for Determining Kinetic Actions The present embodiments described in this patent application and other possible embodiments address a computer-centric challenge or problem with a solution that is necessarily rooted in computer technology and may relate to computer-implemented methods, systems, and electronic devices for collecting sensor data related to kinetic actions of a user and for determining the existence of an ME Event based upon such kinetic actions.

In more detail, kinetic actions performed by or upon an individual may be determined by obtaining sensor data from various data sensors associated with various types of computing devices. In some embodiments, the computing devices may comprise mobile electronic devices configured to be carried and/or worn by an individual. For example, in some embodiments, the mobile electronic devices may include smartphones, tablets, smartwatches (or other wearable electronic devices), or the like. Such mobile electronic devices may include a plurality of data sensors for collecting sensor data related to the mobile electronic device and, thus, related to the individual holding or otherwise supporting the mobile electronic device. For example, the data sensors incorporated for use in various embodiments of the present invention may include the following: (i) accelerometers for measuring the acceleration of the mobile electronic device, (ii) magnetometers for measuring the orientation and/or directional-heading of the mobile electronic device, (iii) gyroscopes for measuring the orientation and/or directional-heading of the mobile electronic device, (iv) location determining elements, such as global positioning system (GPS) elements, for measuring the geolocation of the mobile electronic device, and/or (v) barometers for measuring the atmospheric pressure data and, thus, the height of the mobile electronic device. Although some embodiments may incorporate the use of one or more of the above-described data sensors, it should be understood that other data sensors may also be used.

Embodiments may provide for the data sensors of the mobile electronic device to be used to collect various types of sensor data related to the kinetic actions of the individual holding or otherwise carrying the mobile electronic device. For example, the data sensors may be configured to collect the following types of sensor data: (i) orientation data, (ii) elevation or height data, (iii) positional displacement data, (iv) velocity data, and/or (v) acceleration data. In some embodiments, certain sensor data may be determined from other sensor data. For example, velocity data may be determined by a single integration of acceleration data with respect to time. Similarly, a positional displacement may be determined by a double integration of acceleration data with respect to time. From such sensor data, embodiments provide for the determination of kinetic actions being performed by or upon the individual holding or otherwise supporting the mobile electronic device. For instance, as was described above, examples of such kinetic actions include: (i) the individual's physical body being oriented in a particular manner (e.g., standing upright, leaning, sitting down, lying down, etc.), (ii) a change in the individual's orientation, (iii) the individual being immobilized (i.e., remaining generally motionless), (iii) the individual moving at a particular speed, (v) the individual falling or collapsing (or, more generally, moving under a particular acceleration), (vi) the individual making an impact, such as against an object or the ground, (vii) the individual convulsing (e.g., shaking or trembling), and/or the like.

In more detail, based upon a change in an individual's orientation, as well as sensor data related to the individual's velocity and acceleration, embodiments may determine that the individual has experienced a kinetic action in the form of falling. A specific example of such a kinetic action may include the individual falling or collapsing to the ground from a standing, upright position. For example, at a starting time, the individual may be standing on the ground in an upright position. The data sensors on the individual's mobile electronic device may detect that the mobile electronic device, and thus the individual, is stationary and not undergoing an acceleration. Furthermore, the sensors of the mobile electronic device may detect that the individual is in an upright position based upon the orientation, position, and/or height of the individual holding or otherwise supporting the mobile electronic device. After the starting time, the sensors may detect that the individual undergoes an acceleration in a downward direction for a period of time (a "period of acceleration"). Furthermore, the data sensors of the mobile electronic device may detect that during the period of acceleration, the individual's orientation, position, and/or height has changed from the upright position to a generally horizontal position.

Based upon the individual undergoing the acceleration and/or on the change in the individual's position/orientation, embodiments may determine that the individual underwent a kinetic action in the form of falling (e.g., falling or collapsing to the ground). The determination of the individual experiencing a kinetic action in the form of falling may be further supported by analyzing the characteristics of the collected sensor data. For example, if the acceleration experienced by the individual has a magnitude approximately equal to earth's gravitational acceleration, such as determination may be further indicative of the individual experiencing the kinetic action of falling. Although the above description was primarily with reference to falling from an upright, standing position, a kinetic action of falling may also include falling from significant heights, such as from a ladder or from a building roof.

In addition to the kinetic action of falling, embodiments may also include a kinetic action in the form of an individual experiencing an impact. An example of such an impact may be the individual impacting the ground after falling from an upright standing position. Embodiments may provide for such an impact to be determined based upon the data sensors measuring a deceleration of the individual over a short period of time (the "period of deceleration"). In certain instances, the period of deceleration associated with an impact may be very short, such as less than 2 seconds, less than 1 second, less than 0.5 second, less than 0.25 second, or less than 0.1 second. As such, based upon the quick deceleration, embodiments may determine that the individual has undergone a kinetic action in the form of an impact. Although the above description referenced an impact with the ground after a fall, the kinetic action of making an impact may also include impacting other objects, such as impacting an object while traveling at a high rate of speed or being impacted by an object that is travelling at a high rate of speed.

In certain instances, particularly with respect to impacting the ground, the kinetic action of the impact may include, or may be followed by, a kinetic action in the form of a "bounce." In such a bounce, after the individual initially make an impact with the ground, the direction of motion of the individual may transition from moving towards the ground to moving away from the ground. The individual may reach a maximum distance away from the ground, at which time the direction of motion of the individual may again change by moving back towards the ground. The individual may again impact the ground (less forcefully) and perform additional cycles of directional changes until the individual settles on the ground. Each of such directional/acceleration changes may be detected by the data sensors of the mobile computing device, such that a determination can be made that the individual has experienced a kinetic action in the form of a bounce.

In addition to the kinetic action of an impact, embodiments may include a kinetic action in the form of remaining generally motionless for a period of time ("period of immobility"). Such a kinetic action may be due to the individual being unconscious or otherwise incapacitated. Embodiments may provide for the determination of such a kinetic action to be based upon the data sensors measuring no or little movement of the individual over the period of immobility. In some embodiments, the individual may not be required to be absolutely still to be considered motionless. For example, although the individual may be generally immobile, the individual may, nevertheless, make small involuntary or voluntary movements. Such involuntary movements may be due to convulsions, spasms, tremors, seizures, or the like, whereas voluntary movements may be due to the individual not being completely incapacitated but, nevertheless, unable to entirely control his/her movements. Some embodiments may consider such involuntary or voluntary movements as not affecting the status of the individual being considered generally motionless if such movements are over a distance of less than 10 inches, 8 inches, 5 inches, 4 inches, 3 inches, 2 inches, or 1 inch. Such distances may be measured by the data sensors, such as by the accelerometer, wherefrom collected acceleration data may be twice integrated to determine displacement. Upon the individual remaining generally motionless for at least the period of immobility, embodiments may determine that the individual has undergone a kinetic action in the form of being motionless.

In addition to the kinetic actions described above (i.e., falling, impacting the ground, remaining motionless), embodiments provide for the determination of other kinetic actions performed or experienced by an individual. For example, embodiments may be configured to determine that an individual is undergoing convulsive-type movements, which may be indicative of spasms, tremors, seizures, or the like. Such convulsive-type movements may be determined from the data sensors of the mobile electronic device sensing that the individual is experiencing quick, repetitive changes in acceleration. Such changes in acceleration may be the result of the individual experiencing repetitive directional changes in movement (e.g., a shaking-type movement, a vibrational-type movement, and/or repetitive back-and-forth movement). Such a convulsive-type movement may be periodic or non-periodic, and may be associated with relatively short displacements. For instance, during each part of the convulsive-type movements, the individual may be physically displaced in a particular direction by no more than 1 inch, 0.5 inch, 0.25 inch, 0.1 inch, or 0.01 inch, before beginning another displacement in a different direction.

Embodiments may also provide for the determination of kinetic actions in the form of the individual travelling at certain velocity. For example, for an individual walking at a normal pace, embodiments may determine, based upon velocity data, that the individual is performing a kinetic action in the form of travelling at a slow rate of speed (or travelling at a low velocity). Examples of slow rates of speed may be between 0.1 and 15 miles per hour, 1 and 10 miles per hour, 2 and 6 miles per hour, or 3 and 5 miles per hour. In contrast for an individual driving or riding in a vehicle, embodiments may determine, based upon velocity data, that the individual is performing the kinetic action of travelling at a high rate of speed (or travelling at a high velocity). Examples of high rates of speed may be between 15 and 1000 miles per hour, 20 and 300 miles per hour, 25 and 200 miles per hour, or 30 and 100 miles per hour. As described previously, the velocity of the individual may be determined by calculating a single integral of acceleration data over time.

Exemplary Embodiments for Determining a Medical Emergency Event

Based upon the kinetic actions of the individual, as determined from the sensor data obtained by the mobile electronic device, embodiments may be further configured to determine whether the individual is likely experiencing an ME Event. In some embodiments, the determination of an ME Event will be based upon comparing the determined kinetic actions with models ("Event Models"), which comprise representations of one or more kinetic actions. For instance, some embodiments may include an Event Model in the form of a Sequential-Action Model comprising a representation of a sequence of kinetic actions. Other embodiments may include an Event Model in the form of a Single-Action Model comprising a representation of a single kinetic action.

In more detail, certain embodiments of EM Models may include Sequential-Action Models, with such models comprising a representation of a sequential listing of kinetic actions. For instance, a Sequential-Action Model indicative of a heart attack, stroke, drug overdose, anaphylactic shock, or diabetic episode-type ME Event (a "Collapse sequential model") may include a representation of the following kinetic actions, in sequential order: (1) an individual falling, (2) the individual experiencing an impact, and (3) the individual remaining generally motionless. As such, embodiments can compare kinetic actions obtained by an individual's mobile electronic device with the Collapse sequential model to determine if the individual is experiencing a ME Event in the form of a heart attack, stroke, drug overdose, anaphylactic shock, or diabetic episode. Specifically, if embodiments determines that the kinetic actions experienced by the individual match the sequence of kinetic actions represented by the Collapse sequential model, then embodiments may determine that the individual is likely experiencing an ME Event, such as a heart attack. For example, if embodiments determine, via the individual's mobile electronic device, that the individual undergoes the following kinetic actions in sequential order: (1) the individual falling, (2) the individual experiencing an impact, and (3) the individual remaining generally motionless, then because such kinetic actions match the sequence of kinetic actions of the Collapse sequential model, embodiments may determine that the individual is likely undergoing an ME Event, such as a heart attack.

In some embodiments, the Collapse sequential model may include more, less, or different kinetic actions than those described above. In further embodiments, the Collapse sequential model may require that, in addition to the specific sequence of kinetic actions, the kinetic actions and/or sensor data have specific values, magnitudes, characteristics and/or time-frames. For example, for the kinetic action of the individual falling, the Collapse sequential model may require that the fall be associated with the individual falling to the ground from an upright, standing position. Such a determination may be based upon various criteria. For example, such a determination may be made by analyzing the distance the individual travelled while falling. If the distance travelled by the individual during the period of acceleration corresponds with the distance the individual would likely travel when falling from the upright position to a horizontal position on the ground (e.g., about 2 feet, about 3 feet, about 4 feet, about 5 feet, or the like), then such analysis may support a determination of the individual experiencing the kinetic action of falling to the ground. Embodiments may provide for such a distance to be calculated by performing a double integration of the acceleration value measured for the individual over the period of acceleration.

In addition, for the kinetic action of the individual undergoing an impact, the Collapse sequential model may require that the impact be associated with the individual impacting the ground. Such a determination may be made based upon multiple criteria, such as the individual undergoing an impact with a specified impact force indicative of an impact with the ground after falling from an upright standing position. In some embodiments, such an impact force may be indicative of the individual falling from a particular height, such as from about 2 feet, 3 feet, 4 feet, 5 feet, or 6 feet (i.e., indicative of the individual falling from an upright, standing position to a generally horizontal position on the ground). It is generally understood that the force of an impact corresponds with a change in velocity over an impact period (e.g., the period of deceleration). As such, a significant change in velocity may correspond with a significant impact, such as may result from an impact of the individual falling to the ground from an upright position. Contrastingly, a relatively low change in velocity may correspond to less forceful impact, such as may result from the individual intentionally sitting down or lying down.

In addition to requiring that the force of the impact and/or the change in velocity of the individual during the impact correspond with a ground impact, the Collapse sequential model may require that the kinetic action of the impact include a bounce. As was previously described, a bounce may consist of a number of directional changes made by the individual after impacting the ground. In some embodiments, a maximum distance travelled by the individual in a direction away from the ground during the bounce may be proportional to the impact force initially experienced by the individual during the impact with the ground.

Finally, for the kinetic action of the individual remaining generally motionless, the Collapse sequential model may require that the individual remain generally motionless for a predetermined period of time. Such predetermined period of time may be for at least 5 seconds, at least 10 seconds, at least 15 seconds, or more. Such a predetermined period of time may be indicative of the individual being unconscious or otherwise incapacitated.

Embodiments may include other Sequential-Action Models in addition to the Collapse sequential model described above. For instance, embodiments may also include a Sequential-Action Model representative of a fall from a significant height (a "SF sequential model"). An individual experiencing a sequence of kinetic actions that correspond with such SF sequential model may likely be experiencing an ME Event in the form of fall, which can result in an acute, severe injury. The SF sequential model may include a representation of the following kinetic actions, which are similar to the Collapse sequential model discussed above, namely: (1) an individual falling, (2) the individual experiencing an impact, and (3) the individual remaining generally motionless. Embodiments may compare kinetic actions obtained by an individual's mobile electronic device with the SF sequential model to determine if the individual is experiencing an ME Event due to a fall from a significant height. Specifically, if embodiments determines that the kinetic actions experienced by the individual match the sequence of kinetic actions represented by the SF sequential model, then embodiments may determine that the individual is likely experiencing an ME Event, such as a significant fall. For example, if embodiments determines, via the user's mobile electronic device, that the individual undergoes, in sequential order, the following kinetic actions: (1) the individual falling more than a minimum distance, (2) the individual impacting the ground, and (3) the individual remaining generally motionless, then embodiments may determine that the individual is undergoing an ME Event resulting from a fall from a significant height.

In some embodiments, the SF sequential model may include more, less, or different kinetic actions than those described above. As with the Collapse sequential model, the SF sequential model may require that, in addition to the specific sequence of kinetic actions, the kinetic actions and/or sensor data have specific values, magnitudes, characteristics and/or time-frames. For example, the SF sequential model may require that during the kinetic action of falling, the individual falls a significant minimum distance. Such a significant minimum distance may be, for instance, at least 5 feet, 10 feet, 15 feet, at least 20 feet, or more. Such a significant minimum distance may correspond to the individual falling from significant height, such as from a ladder, from a building roof, or the like. The distance fallen by the individual may be determined by performing a double integration of the acceleration of the individual over the acceleration period.

Additionally, the SF sequential model may require that during the kinetic action of making an impact, the individual must make an impact with a particular impact force, which is indicative of an impact with the ground after falling from a significant height (e.g., from at least 5 feet, 10 feet, 15 feet, 20 feet, or more). Similarly, the SF sequential model may require that during the kinetic action of making an impact, the individual also undergo a bounce, as was previously described. In some embodiments, a maximum distance travelled by the individual in a direction away from the ground during such bounce may be proportional to the impact force of the individual initially impacting the ground after the fall.

Furthermore, the SF sequential model may require that for the kinetic action of the individual remaining generally motionless, the SF sequential model may require that the individual remain generally motionless for a predetermined period of time (e.g., at least 5 seconds, 10 seconds, 15 seconds, or more). Such a predetermined period of time may be indicative of the individual being unconscious or otherwise incapacitated.

Embodiments may also include a Sequential-Action Model representative of a high-velocity impact (a "HVI sequential model"). The HVI sequential model may be indicative of an individual experiencing an ME Event in the form of an impact after traveling at a high velocity, which may result in an acute, severe injury. The HVI sequential model may comprise a representation of the following kinetic actions, in sequential order: (1) an individual traveling at a high velocity, (2) the individual experiencing an impact, and (3) the individual remaining generally motionless. As such, embodiments may compare an individual's kinetic actions, as obtained by the individual's mobile electronic device, with the HVI sequential model to determine if the individual is experiencing a ME Event in the form of a high-velocity impact.

Specifically, if embodiments determines that the kinetic actions experienced by the individual match the sequence of kinetic actions represented by the HVI sequential model, then embodiments may determine that the individual is likely experiencing an ME Event in the form of a high-velocity impact. For example, if embodiments determines that the individual undergoes, in sequential order, the following kinetic actions: (1) the individual travelling at a high velocity, (2) the individual making a high-velocity impact, and (3) the individual remaining generally motionless, then embodiments may determine that the individual is undergoing am ME Event in the form of a high-velocity impact.

In some embodiments, the HVI sequential model may include more, less, or different kinetic actions than those described above. As with the previously-discussed Sequential-Action Models, the HVI sequential model may require that, in addition to the specific sequence of kinetic actions, the kinetic actions and/or sensor data have specific values, magnitudes, characteristics and/or time-frames. In some embodiments, the HVI sequential model may require that during the kinetic action of traveling at a high velocity includes the individual travelling at least at a minimum speed. Such minimum speed may be, for instance, at least 10 miles per hour, 15 miles per hour, 20 miles per hour, 25 miles per hour, or more. Similarly, the HVI sequential model may require that the kinetic action of the individual making the high-velocity impact make such an impact with at least a minimum impact force. Furthermore, for the kinetic action of the individual remaining generally motionless, the HVI sequential model may require that the individual remain generally motionless for a period of time (e.g., at least 5 seconds, at least 10 seconds, etc.). Such a period of time may be indicative of the individual being unconscious or otherwise incapacitated.

In addition to the sequential models, such as those described above, embodiments may be used to determine the existence of an ME Event based upon a Single-Action Model. An example of a Single-Action Model may include a convulsive model. Such a convulsive model may be indicative of an individual undergoing an ME Event in the form of epileptic seizures, spasms, tremors, or the like. The convulsive model may comprise a representation of a kinetic action in the form of quick, convulsive-type movements of the individual's body for a period of time (the "convulsive period"). In some embodiments, the convulsive model may require that the convulsive period be at least 5 seconds, at least 10 seconds, or more. Additionally, in some embodiments, the convulsive model may require that the convulsive-type movements have specific frequencies and/or may cause specific, repetitive positional displacements of the individual's body. For example, in some embodiments, the positional displacements of the individual's body during a convulsive-type movement may be less than about 1 inch, less than 0.5 inch, less than 0.25 inch, less than 0.1 inch, or less than 0.01 inch. Embodiments can compare kinetic actions obtained by an individual's mobile electronic device with the convulsive model to determine if the individual is experiencing an ME Event due an epileptic seizure, spasm, tremor, or the like.

Specifically, if embodiments determines that the kinetic action experienced by the individual matches the kinetic actions represented by the convulsive model, then embodiments may determine that the individual is likely experiencing an ME Event in the form of an epileptic seizure, spasm, tremor, or the like. For example, if embodiments determines, via the user's mobile electronic device, that the individual undergoes a kinetic action in the form of convulsive-type movements for a particular period of time (i.e., the convulsive period), then embodiments may determine that the individual is undergoing an ME Event resulting from an epileptic seizure, spasm, tremor, or the like.

Another example of a Single-Action model may include an isolated-impact model. Such an isolated-impact model may be indicative of an individual undergoing an ME Event in the form of an isolated impact, which may result in an acute severe injury. An example of such an isolated impact may include a non-moving impact resulting from the individual being hit as a pedestrian by a large and/or fast moving object, such as a vehicle. The isolated-impact model may require that the individual experience an impact that satisfies at least a minimum impact force. Such a minimum impact force may be indicative of the individual being impacted by a large and/or fast-moving object, such as a vehicle. In some embodiments, the isolated-impact model may further require that the individual not be moving, or be moving relatively slowly, in the moments immediately prior to the impact. Such slow or non-movement may be indicative of the individual being impacted by a moving object, as opposed to the individual making an impact with another object while the individual is travelling at a high speed (i.e., as would be involved in a high-velocity impact). Embodiments can compare kinetic actions obtained by an individual's mobile electronic device with the isolated-impact model to determine if the individual is experiencing an ME Event due to an isolated impact.

Specifically, if embodiments determines that the kinetic action experienced by the individual matches the kinetic action represented by the isolated-impact model, then embodiments may determine that the individual is likely experiencing an ME Event in the form of an isolated impact. For example, if embodiments determines, via the user's mobile electronic device, that the individual undergoes a kinetic action in the form of a quick change in acceleration that includes a high impact force, then embodiments may determine that the individual is undergoing an ME Event resulting from a sudden impact.

Embodiments provide for the ME Models to be predetermined and pre-set. However, in some embodiments, the ME Models may be continually developed and refined as sensor data and kinetic actions are obtained by individual users of the present invention. For instance, various embodiments may utilize machine learning programs or techniques to recognize ME Events from kinetic actions. The programs may include curve fitting, regression model builders, convolutional or deep learning neural networks, pattern recognition techniques, or the like. Moreover, automated data analysis and machine learning environments may, in certain embodiments, assist in ME Event analysis and detection. For instance, for heart attack-type ME Events, embodiments may continually refine the value or magnitude of representative kinetic actions that do or do not indicate the likelihood of a heart attack-type ME Event.

As a particular example, some embodiments of the Collapse sequential model require that the impact force of the kinetic action of the individual impacting the ground satisfy a minimum magnitude before a determination can be made that the individual's kinetic actions match the Collapse sequential model, so as to indicate that the individual is likely undergoing a heart attack-type ME Event. As more individuals use embodiments of the present invention, and as more sensor data and kinetic actions are analyzed from such individuals, the minimum magnitude of the impact force indicative of an individual impacting the ground during a heart attack-type ME Event can be continually refined. As such, as embodiments of the present invention continues to collect sensor data related to kinetic actions of individuals, the Event Models can be more accurately specified.

Furthermore, as will be discussed in more detail below, in some embodiments, individuals may be required to provide individual profile data, which may include medical information. The medical information may include information relevant to the individual's previous medical history, such as history of heart disease, high-blood pressure, drug use, allergies, diabetes, epilepsy, and the like. In some embodiments, the determination of whether an individual is undergoing an ME Event may be based, at least in part, on the individual's medical information. For instance, some embodiments may specify that even if an individual's kinetic actions match an ME model, the determination as to whether the individual is experiencing an ME Event may further require that the individual has a requisite medial history. As an example, an individual may undergo kinetic actions that match the Collapse sequential model. However, certain embodiments may not make a determination that the individual has experienced an ME Event unless the individual has a medical history that includes heart disease, high-blood pressure, or the like.

Exemplary Embodiments for Contacting Emergency Services

Upon a determination that an individual is likely undergoing an ME Event, embodiments may provide for EM Responders to be contacted so as to provide the individual with EM Services. In more detail, upon an ME Event even being detected, embodiments provide for an alert message (e.g., a push notification, email, text, or other alert message) to be provided to the individual, with such alert message indicating the detection of an ME Event and, further, inquiring as to whether the individual requires EM Services. In some embodiments, the alert message may be provided via a graphic display of the individual's mobile electronic device. For example, the alert message may be provided in the form of a graphical dialogue box that includes a health status question in the form of: "A medical emergency has been detected—Do you need immediate medical assistance?" The alert message may include one or more predetermined answer interfaces, which may be presented as graphically-selectable buttons, check boxes, or the like (collectively "answer interfaces"). For instance, the alert message may include a "yes" answer interface, which is indicative of the individual answering that he/she is in need of immediate EM Services, and a "no" answer interface, which is indicative of the individual answering that he/she is not in need of EM Services.

Upon the individual selecting the "yes" answer indicator in response to the health status question, the mobile electronic device may connect with EM Responders (or to dispatchers of the EM Responders) to request EM Services to be provided to the individual. In some embodiments, the connection may be over a voice communications network, such as a cellular communications network to which the individual's mobile electronic device may be connected. Via the voice communications network, the individual may personally communicate with the EM Responders, or the mobile electronic device may provide an automated request message to the EM Responders indicating that the individual has experienced a ME Event and is need of immediate EM Services. In other embodiments, the request message may be sent by other methods of data communications, such as by SMS text messaging, email messaging, or the like.

In certain embodiments in which an automated request message is sent to the EM Responders, the automated request message may include information relevant to the individual experiencing the ME Event. For example, in some embodiments, the request message may include the individual's name, health history information, and current location. To facilitate the provision of such information to the EM Responders, in some embodiments, the individual may be required to upload individual profile data to the individual's mobile electronic device and/or to other computing devices that may be included within certain embodiments of the present invention.

Such individual profile data may include personal information, medical information, and/or contact information. The personal information may include information such as the individual's name, age, sex, height, weight, and the like. The medical information may include information relevant to the individual's previous medical history, such as history of heart disease, high-blood pressure, drug use, allergies, diabetes, epilepsy, etc. Such information may be provided so that the EM Responders can provide appropriate EM Services to the individual. The contact information may be the individual's home address, work address, telephone number, next of kin, or the like.

In some embodiments, contact information provided by the individual may be used by the EM Responders as the location to which to travel to for purposes of providing EM Services to the individual. Alternatively, in some embodiments, the individual's mobile electronic device may provide the individual's current geolocation, which is obtained from the location determining element (i.e., GPS) of the mobile electronic device. As such, EM Responders will have the requisite geolocation information necessary to travel to the individual's location so as to provide EM Services to the individual.

Should the individual select the "no" answer indicator in response to the health status question or push notification, the mobile electronic device may perform no further actions. Specifically, because the individual indicated that the individual was not experiencing a ME Event and was not in need of medical attention, EM Responders may not be contacted.

As a further alternative, should the individual fail to provide an answer to the health status question within a predefined period of time, such as within 5 seconds, 10 seconds, 15 seconds, within 20 seconds, or some other timer period, the mobile electronic device may automatically connect with EM Responders to request EM Services for the individual. Specifically, the individual failing to provide an answer to the alert message may be indicative of the individual being unconscious or otherwise incapacitated, such that the individual is not capable of providing an answer to the alert message. As such, embodiments may be configured to automatically connect with EM Responders to request EM Services for the individual, as was previously described.

Specific embodiments of the technology will now be described in connection with the attached drawing figures. The embodiments are intended to describe aspects of the invention in sufficient detail to enable those skilled in the art to practice the invention. Other embodiments may be utilized and changes may be made without departing from the scope of the present invention. The following detailed description is, therefore, not to be taken in a limiting sense. The scope of the present invention is defined only by the appended claims, along with the full scope of equivalents to which such claims are entitled.

Exemplary Mobile Electronic Device

Figure 1:
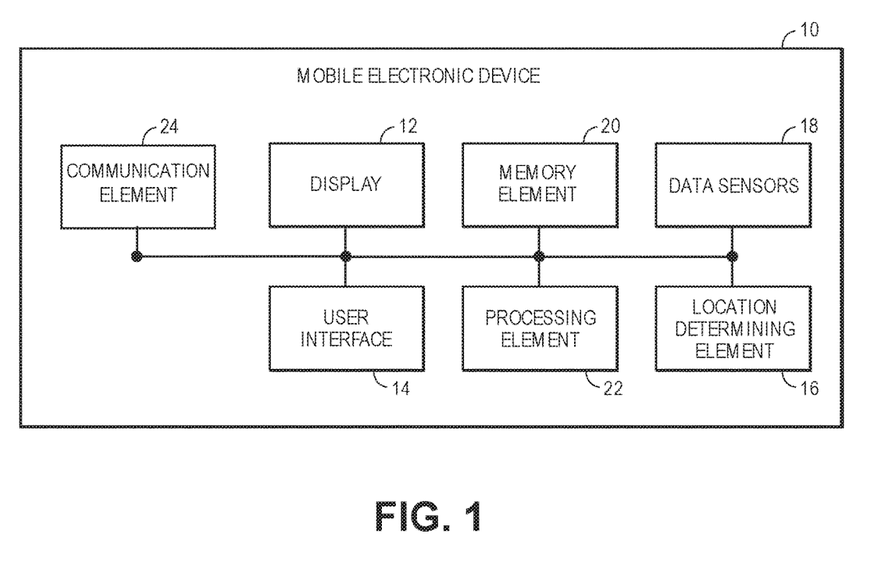
FIG. 1 illustrates various components of an exemplary mobile electronic device shown in block schematic form.
Figure 2:
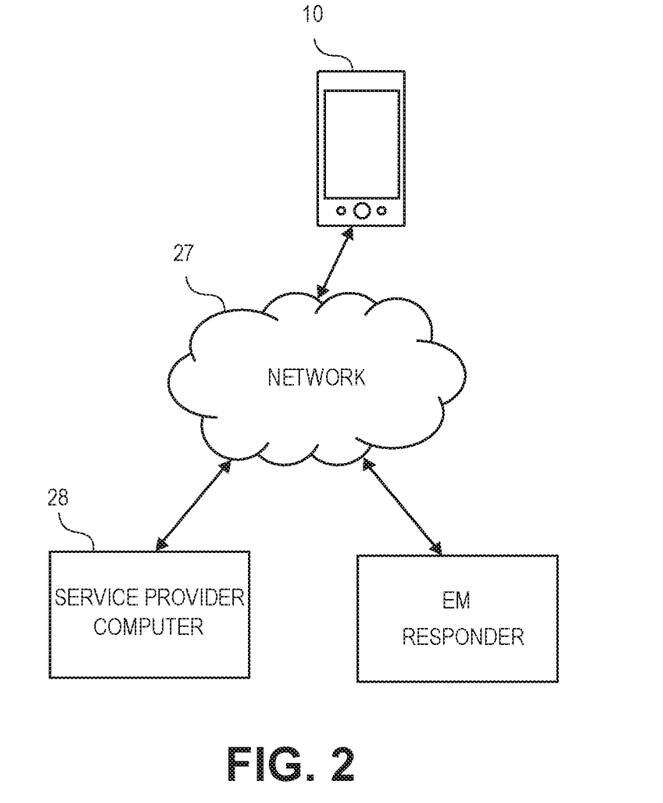
FIG. 2 illustrates various components of an exemplary system for detecting medical emergency events shown in block schematic form.

FIG. 1 depicts an embodiment of an exemplary mobile electronic device 10 for use in determining whether an individual is experiencing an ME Event. The mobile electronic device 10 may be embodied as a smartphone, a tablet computer, a laptop computer, a phablet, smart glasses, a smartwatch, wearable electronics, or the like, and may, as illustrated in FIG. 2, broadly comprise a display 12, a user interface 14, a location determining element 16, one or more data sensors 18, a memory element 20, and a processing element 22. The mobile electronic device 10 may also include a communication element 24 configured as one or more transceivers that utilize radio frequency (RF) communication, such as cellular, WiFi, Bluetooth™, or the like, to communicate with other devices, systems, or networks.

The display 12 may include video devices of the following types: plasma, light-emitting diode (LED), organic LED (OLED), Light Emitting Polymer (LEP) or Polymer LED (PLED), liquid crystal display (LCD), thin film transistor (TFT) LCD, LED side-lit or back-lit LCD, heads-up displays (HUDs), or the like, or combinations thereof. The display 12 may include a screen on which the information is presented, with the screen possessing a square or a rectangular aspect ratio that may be viewed in either a landscape or a portrait mode. In various embodiments, the display 12 may also include a touch screen occupying the entire screen or a portion thereof so that the display 12 functions as part of the user interface 14. The touch screen may allow the user to interact with the mobile electronic device 10 by physically touching, swiping, or gesturing on areas of the screen.

The user interface 14 generally allows the user to utilize inputs and outputs to interact with the mobile electronic device 10. Inputs may include buttons, pushbuttons, knobs, jog dials, shuttle dials, directional pads, multidirectional buttons, switches, keypads, keyboards, mice, joysticks, microphones, or the like, or combinations thereof. Outputs may include audio speakers, lights, dials, meters, printers, or the like, or combinations thereof. With the user interface 14, the user may be able to control the features and operation of the display 12. For example, the user may be able to zoom in and out on the display 12 using either virtual onscreen buttons or actual pushbuttons. In addition, the user may be able to pan the image on the display 12 either by touching and swiping the screen of the display 12 or by using multidirectional buttons or dials.

The location determining element 16 generally determines a current geolocation of the mobile electronic device 10 and may receive and process radio frequency (RF) signals from a global navigation satellite system (GNSS) such as the global positioning system (GPS) primarily used in the United States, the GLONASS system primarily used in the Soviet Union, or the Galileo system primarily used in Europe. The location determining element 16 may accompany or include an antenna to assist in receiving the satellite signals. The antenna may be a patch antenna, a linear antenna, or any other type of antenna that may be used with location or navigation devices. The location determining element 16 may include satellite navigation receivers, processors, controllers, other computing devices, or combinations thereof, and memory. The location determining element 16 may process a signal, referred to herein as a "location signal", from one or more satellites that includes data from which geographic information such as the current geolocation is derived. The current geolocation may include coordinates, such as the latitude and longitude, of the current location of the mobile electronic device 10. The location determining element 16 may communicate the current geolocation to the processing element 22, the memory element 20, or both.

Although embodiments of the location determining element 16 may include a satellite navigation receiver, it will be appreciated that other location-determining technology may be used. For example, cellular towers or any customized transmitting radio frequency towers may be used instead of satellites may be used to determine the location of the mobile electronic device 10 by receiving data from at least three transmitting locations and then performing basic triangulation calculations to determine the relative position of the device with respect to the transmitting locations. With such a configuration, any standard geometric triangulation algorithm may be used to determine the location of the mobile electronic device. The location determining element 16 may also include or be coupled with a pedometer, accelerometer, compass, or other dead-reckoning components which allow it to determine the location of the mobile computing device 10. The location determining element 16 may determine the current geographic location through a communications network, such as by using Assisted GPS (A-GPS), or from another electronic device. The location determining element 16 may even receive location data directly from a user.

The data sensors 18 generally detect the position, orientation, speed, and acceleration of the mobile computing device 10 and, thus, the individual holding or otherwise supporting the mobile electronic device. The data sensors 18 may be selected from one or more of the following sensors: (i) accelerometers, (ii) magnetometers, (iii) gyroscopes, and/or (iv) barometers. The accelerometer may be used to measure linear acceleration relative to a frame of reference, and thus, can be used to detect motion of the mobile electronic device 10 as well as to detect an angle or orientation of the mobile electronic device 10 relative to the horizon or ground. By calculating an integral of a measured acceleration with respect to time, embodiments may use data obtained by the accelerometer to measure a velocity of the mobile electronic device 10. Similarly, by calculating a double integral of a measured acceleration with respect to time, embodiments may use data obtained by the accelerometer to measure a displacement distance of the mobile electronic device.

The magnetometer may be used as a compass to determine a direction of magnetic north and bearings of the mobile electronic device 10 relative to magnetic north. The gyroscope may be used to detect both vertical and horizontal orientation of the mobile electronic device 10, and together with the accelerometer and magnetometer may be used to obtain very accurate information about the orientation of the mobile computing device 10. The barometer may be used to detect both a pressure of the atmosphere in which the mobile electronic device 10 is positioned. As such, the barometer may be used to measure altitudes and heights, as well as to measure changes in altitudes and heights. In some additional embodiments, the location determining element 16 may be included as a data sensors 18. Although some embodiments may incorporate the use of one or more of the above-described sensors for the data sensors 18 of the mobile electronic device 10, it should be understood that other sensors may also be used.

The memory element 20 may include one or more electronic hardware data storage components such as read-only memory (ROM), programmable ROM, erasable programmable ROM, random-access memory (RAM) such as static RAM (SRAM) or dynamic RAM (DRAM), cache memory, hard disks, floppy disks, optical disks, flash memory, thumb drives, universal serial bus (USB) drives, or the like, or combinations thereof. In some embodiments, the memory element 20 may be embedded in, or packaged in the same package as, the processing element 22. The memory element 20 may include, or may constitute, a "computer-readable medium." The memory element 20 may store the instructions, code, code segments, software, firmware, programs, applications, apps, services, daemons, or the like that are executed by the processing element 22.

The processing element 22 may include one or more electronic hardware components such as processors, microprocessors (single-core and multi-core), microcontrollers, digital signal processors (DSPs), field-programmable gate arrays (FPGAs), analog and/or digital application-specific integrated circuits (ASICs), or the like, or combinations thereof. The processing element 22 may generally execute, process, or run instructions, code, code segments, software, firmware, programs, applications, apps, processes, services, daemons, or the like. The processing element 22 may also include hardware components such as finite-state machines, sequential and combinational logic, and other electronic circuits that may perform the functions necessary for the operation of the current invention. The processing element 22 may be in communication with the other electronic components through serial or parallel links that include address busses, data busses, control lines, and the like.

The various processes, functions, and features of embodiments of the present invention discussed herein may be performed by the processing element 22 of the mobile computing device 10 carrying out instructions of a computer program, software, firmware, or combinations thereof stored on the memory element 20. In some embodiments, the computer program may be in the form of a mobile "app."

For instance, the processing element 22 may be programmed or configured to perform the following functions. The processing element 22 may be configured to obtain sensor data from one or more of the data sensors 18 of the mobile electronic device 10. The processing element 22 may be configured to analyze the sensor data to determine kinetic actions of the individual carrying or otherwise holding the mobile electronic device 10. The processing element 22 may also be configured to compare the kinetic actions with one or more Event Models to determine if the individual is likely undergoing an ME Event. Furthermore, the processing element 22 may be configured to transmit communications via the communication element 24 to EM Responders to request EM Services for the individual.

Exemplary Service Provider Computer and Network

FIG. 2 depicts exemplary embodiments of a system, which may be utilized for detecting ME Events. The system may include a network 27 and a service provider computer 28, in addition to mobile electronic device 10. In such embodiments, the various processes, functions, and features of embodiments of the present invention discussed herein may be performed in part by the service provider 28 and/or in part (or entirely) by the mobile computing device 10. For example, the mobile computing device 10 may be configured to obtain sensor data from the data sensors 18 and to provide such sensor data to the service provider computer 28 via the network 27. The service provider computer 28 may, thus, be configured to execute instructions of a computer program, software, firmware, or combinations thereof to analyze the sensor data to determine kinetic actions and to detect ME Events.

In some alternative embodiments, the mobile computing device 10 may be configured to perform all processes, functions, and features described herein by carrying out the instructions of a computer program and/or software that is downloaded from the service provider computer 28 via the network 27. Such computer program and/or software may be updated from time to time by the mobile electronic device 10 downloading updates and/or new versions for the computer program and/or software from the service provider computer 28. For example, the service provider computer 28 may store updates of the Event Models, such as may be determined by curve fitting, regression model builders, convolutional or deep learning neural networks, pattern recognition techniques, or the like. Such updated Event Models may be periodically provided to the mobile electronic device 10 over the network 27, such that the mobile electronic device 10 can compare a user's kinetic actions with the most current Event Models.

The network 27 may generally allow communication between the mobile electronic device 10 and the service provider computer 28, such as via wireless communication or data transmission over one or more radio links or wireless communication channels. The network 27 may also provide communication between the mobile electronic device 10 and/or the service provider computer 28 and EM Responders (and/or the dispatchers for EM Responders). The network 27 may include local area networks, metro area networks, wide area networks, cloud networks, the Internet, cellular networks, plain old telephone service (POTS) networks, and the like, or combinations thereof. The network 27 may be wired, wireless, or combinations thereof and may include components such as modems, gateways, switches, routers, hubs, access points, repeaters, towers, and the like. The mobile electronic device 10 generally connects to the network 27 wirelessly, such as radio frequency (RF) communication using wireless standards such as cellular 2G, 3G, or 4G, Institute of Electrical and Electronics Engineers (IEEE) 802.11 standards such as WiFi, IEEE 802.16 standards such as WiMAX, Bluetooth®, or combinations thereof.

The service provider computer 28 generally retains electronic data and may respond to requests to retrieve data as well as to store data. In some embodiments, the service provider computer 28 may also perform certain of the processes, functions, and features described herein with respect to detecting ME Events by executing portions, or the entirety, of the computer program and/or software of embodiments of the present invention. The service provider computer 28 may be embodied by a personal computer such as a desktop workstation and/or laptop computer, and/or by application servers, database servers, file servers, gaming servers, mail servers, print servers, web servers, or the like, or combinations thereof. Furthermore, the service provider computer 28 may include a plurality of servers, virtual servers, or combinations thereof. The service provider computer 28 may be configured to include or execute software such as file storage applications, database applications, email or messaging applications, web server applications, or the like, in addition to and/or in conjunction with the computer program and/or software described elsewhere herein.

Figure 3:
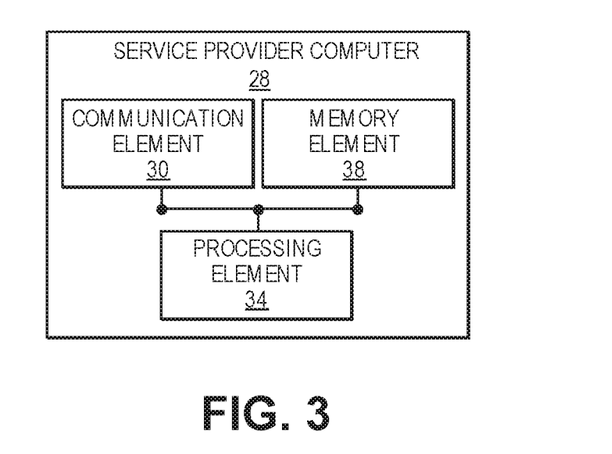
FIG. 3 illustrates various components of an exemplary service provider computer shown in block schematic form.

The service provider computer 28 may include a communication element 30, a processing element 34, and a memory element 38. The communication element 30 generally allows communication with external systems or devices. The communication element 30 may include signal or data transmitting and receiving circuits, such as antennas, transceivers, amplifiers, filters, mixers, oscillators, digital signal processors (DSPs), and the like. The communication element 30 may establish communication wirelessly by utilizing RF signals and/or data that comply with communication standards such as cellular 2G, 3G, or 4G, IEEE 802.11 standard such as WiFi, IEEE 802.16 standard such as WiMAX, Bluetooth™, or combinations thereof. Alternatively, or in addition, the communication element 30 may establish communication through connectors or couplers that receive metal conductor wires or cables which are compatible with networking technologies such as ethernet. In certain embodiments, the communication element 30 may also couple with optical fiber cables. The communication element 30 may be in communication with or electronically coupled to memory element 38 and/or processing element 34.

The memory element 38 may include data storage components such as read-only memory (ROM), programmable ROM, erasable programmable ROM, random-access memory (RAM) such as static RAM (SRAM) or dynamic RAM (DRAM), cache memory, hard disks, floppy disks, optical disks, flash memory, thumb drives, USB ports, or the like, or combinations thereof. The memory element 38 may include, or may constitute, a "computer-readable medium". The memory element 38 may store the instructions, code, code segments, software, firmware, programs, applications, apps, services, daemons, or the like that are executed by the processing element 34. The memory element 38 may also store settings, data, documents, sound files, photographs, movies, images, databases, and the like.

The processing element 34 may include processors, microprocessors, microcontrollers, DSPs, field-programmable gate arrays (FPGAs), analog and/or digital application-specific integrated circuits (ASICs), or the like, or combinations thereof. The processing element 34 may generally execute, process, or run instructions, code, code segments, software, firmware, programs, applications, apps, processes, services, daemons, or the like. The processing element 34 may also include hardware components, such as finite-state machines, sequential and combinational logic, and other electronic circuits that may perform the functions necessary for the operation of embodiments of the current inventive concept. The processing element 34 may be in communication with the other electronic components through serial or parallel links that include address busses, data busses, control lines, and the like.

Exemplary Computer-Implemented Method

Figure 4:
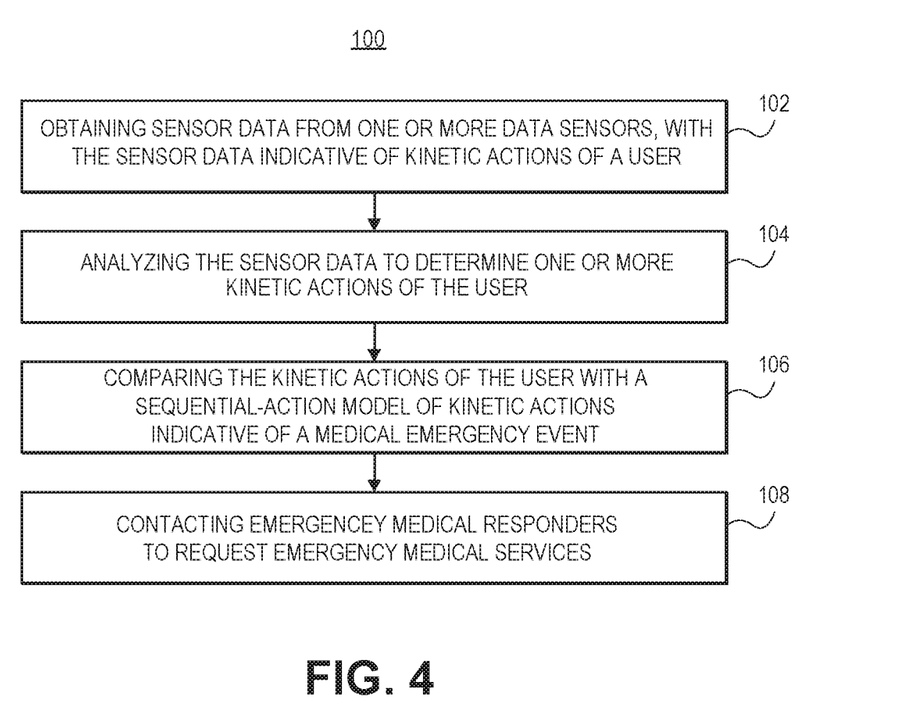
FIG. 4 illustrates an exemplary computer-implemented method of detecting medical emergency events in accordance with aspects of the present embodiments.

FIG. 4 depicts an exemplary computer-implemented method 100 for detecting ME Events. The steps may be performed in the order shown in FIG. 4, or they may be performed in a different order. Furthermore, some steps may be performed concurrently as opposed to sequentially. In addition, some steps may be optional. The steps of the computer-implemented method may be performed by a processing element of the mobile electronic device, by a processing element of the service provider computer, and/or one or more local or remote processors.

A first step 102 of the method 100 may include obtaining sensor data from one or more data sensors of a mobile computing device, with such sensor data indicative of kinetic actions of a user. For example, in some embodiments, the one or more data sensors may comprise an accelerometer configured to obtain sensor data in the form of acceleration data of the user. A next step 104 of the method 100 may include analyzing the sensor data to determine one or more kinetic actions of the user. Examples of such kinetic actions may include, for instance, (1) the user falling to the ground, (2) the user impacting the ground, and/or (3) the user remaining generally motionless. A next step 106 of the method 100 may include comparing the kinetic actions of the user with a Sequential-Action Model of kinetic actions indicative of an ME Event. A Sequential-Action Model may representative of particular sequence of kinetic actions. Examples of such ME Events include heart attacks, strokes, seizures, falls, accidents, or the like. If the kinetic actions of the user are determined to correspond with the Sequential-Action Model, a next step 108 may include contacting emergency services to request medical assistance for the user. The flow of FIG. 4 may include additional, less, or alternate actions, including those discussed elsewhere herein.

Another Exemplary Computer-Implemented Method

Figure 5:
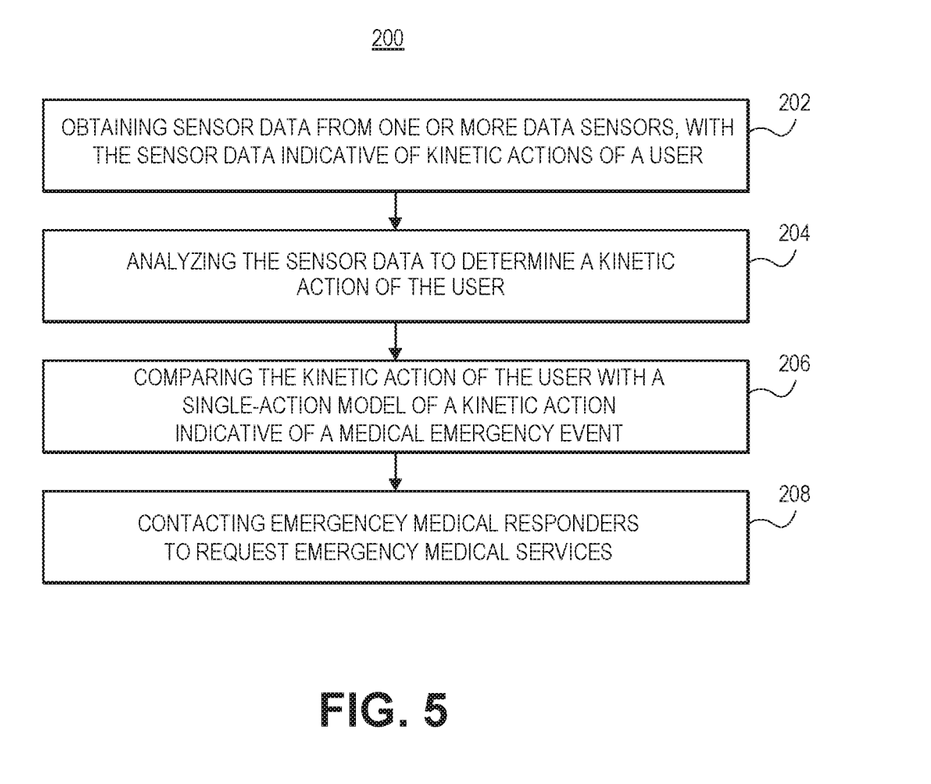
FIG. 5 illustrates an additional exemplary computer-implemented method of detecting medical emergency events in accordance with aspects of the present embodiments.

FIG. 5 depicts another exemplary computer-implemented method 200 for detecting medical emergency events. The steps may be performed in the order shown in FIG. 5, or they may be performed in a different order. Furthermore, some steps may be performed concurrently as opposed to sequentially. In addition, some steps may be optional. The steps of the computer-implemented method may be performed by a processing element of the mobile electronic device, by a processing element of the service provider computer, and/or one or more local or remote processors.

A first step 202 of the method 200 may include obtaining sensor data from one or more data sensors of a mobile computing device, with such data indicative of kinetic actions of a user. For example, in some embodiments, the one or more sensors may comprise an accelerometer configured to obtain sensor data in the form of acceleration data of the user. A next step 204 of the method 200 may include analyzing the data to determine a kinetic action of the user. Examples of such kinetic actions may include, for instance (1) the user undergoing a convulsion, or (2) the user experiencing an isolated impact. A next step 206 of the method 200 may include comparing the kinetic action of the user with a Single-Action Model of a kinetic action indicative of an ME Event. A Single-Action Model may be representative of particular kinetic actions. Examples of such ME Events include seizures, a sudden impact with a vehicle, or the like. If the kinetic action of the user is determined to correspond with the Single-Action Model, a next step 208 of the method 200 may include contacting EM Responders to request EM Services for the user. The flow of FIG. 5 may include additional, less, or alternate actions, including those discussed elsewhere herein.

Exemplary Computer Systems

In one aspect, a computer system configured to detect medical emergency events may be provided. The computer system may include one or more processors, servers, transceivers, and/or sensors configured to: (1) obtain or receive sensor data generated from one or more sensors indicative of kinetic actions of a user (such as via wireless communication or data transmission over one or more radio frequency links or digital communication channels); (2) analyze the sensor data to associate the sensor data with one or more kinetic actions of the user; (3) compare the one or more kinetic actions of the user with a model of kinetic actions to determine whether the one or more kinetic actions correspond with the model of kinetic actions, wherein the model of kinetic actions is indicative of a medical emergency event; and/or (4) upon determining that the one or more kinetic actions correspond with the model of kinetic actions, contact, via wireless communication or data transmission over one or more radio links or digital communication channels, medical emergency responders to request medical emergency services for the user.

In another aspect, a computer system configured to detect medical emergency events may be provided. The computer system may include one or more processors, servers, sensors, and/or transceivers configured to: (1) obtain or receive sensor data generated from one or more sensors indicative of kinetic actions of a user (such as via wireless communication or data transmission over one or more radio frequency links or digital communication channels); (2) analyze the sensor data to associate the sensor data with one or more kinetic actions of the user; (3) compare the one or more kinetic actions of the user with a sequential-action model of kinetic actions to determine whether the one or more kinetic actions correspond with the sequential-action model, wherein the sequential-action model is indicative of a medical emergency event; and/or (4) upon determining that the one or more kinetic actions correspond with the sequential-action model, contacting, via wireless communication or data transmission over one or more radio links or digital communication channels, medical emergency responders to request medical emergency services for the user.

In another aspect, a computer system configured to detect medical emergency events may be provided. The computer system may include one or more processors, sensors, transceivers, and/or servers configured to: (1) obtain or receive sensor data generated by one or more sensors indicative of kinetic actions of a user (such as via wireless communication or data transmission over one or more radio links or digital communication channels); (2) analyze the sensor data to associate the sensor data with a kinetic action of the user; (3) compare the kinetic action of the user with a single-action model of kinetic actions to determine whether the kinetic action corresponds with the single-action model, wherein the single-action model is indicative of a medical emergency event; and/or (4) upon determining that the kinetic action corresponds with the single-action model, contact, via wireless communication or data transmission over one or more radio links or digital communication channels, medical emergency responders to request medical emergency services for the user.

The foregoing computer systems may include additional, less, or alternate functionality, including that discussed elsewhere herein.

ADDITIONAL CONSIDERATIONS

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology may include a variety of combinations and/or integrations of the embodiments described herein.

Although the present application sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as computer hardware that operates to perform certain operations as described herein.

In various embodiments, computer hardware, such as a processing element, may be implemented as special purpose or as general purpose. For example, the processing element may comprise dedicated circuitry or logic that is permanently configured, such as an application-specific integrated circuit (ASIC), or indefinitely configured, such as an FPGA, to perform certain operations. The processing element may also comprise programmable logic or circuitry (e.g., as encompassed within a general-purpose processor or other programmable processor) that is temporarily configured by software to perform certain operations. It will be appreciated that the decision to implement the processing element as special purpose, in dedicated and permanently configured circuitry, or as general purpose (e.g., configured by software) may be driven by cost and time considerations.

Accordingly, the term "processing element" or equivalents should be understood to encompass a tangible entity, be that an entity that is physically constructed, permanently configured (e.g., hardwired), or temporarily configured (e.g., programmed) to operate in a certain manner or to perform certain operations described herein. Considering embodiments in which the processing element is temporarily configured (e.g., programmed), each of the processing elements need not be configured or instantiated at any one instance in time. For example, where the processing element comprises a general-purpose processor configured using software, the general-purpose processor may be configured as respective different processing elements at different times. Software may accordingly configure the processing element to constitute a particular hardware configuration at one instance of time and to constitute a different hardware configuration at a different instance of time.

Computer hardware components, such as communication elements, memory elements, processing elements, and the like, may provide information to, and receive information from, other computer hardware components. Accordingly, the described computer hardware components may be regarded as being communicatively coupled. Where multiple of such computer hardware components exist contemporaneously, communications may be achieved through signal transmission (e.g., over appropriate circuits and buses) that connect the computer hardware components. In embodiments in which multiple computer hardware components are configured or instantiated at different times, communications between such computer hardware components may be achieved, for example, through the storage and retrieval of information in memory structures to which the multiple computer hardware components have access. For example, one computer hardware component may perform an operation and store the output of that operation in a memory device to which it is communicatively coupled. A further computer hardware component may then, at a later time, access the memory device to retrieve and process the stored output. Computer hardware components may also initiate communications with input or output devices, and may operate on a resource (e.g., a collection of information).

The various operations of example methods described herein may be performed, at least partially, by one or more processing elements that are temporarily configured (e.g., by software) or permanently configured to perform the relevant operations. Whether temporarily or permanently configured, such processing elements may constitute processing element-implemented modules that operate to perform one or more operations or functions. The modules referred to herein may, in some example embodiments, comprise processing element-implemented modules.

Similarly, the methods or routines described herein may be at least partially processing element-implemented. For example, at least some of the operations of a method may be performed by one or more processing elements or processing element-implemented hardware modules. The performance of certain of the operations may be distributed among the one or more processing elements, not only residing within a single machine, but deployed across a number of machines. In some example embodiments, the processing elements may be located in a single location (e.g., within a home environment, an office environment or as a server farm), while in other embodiments the processing elements may be distributed across a number of locations.

Unless specifically stated otherwise, discussions herein using words such as "processing," "computing," "calculating," "determining," "presenting," "displaying," or the like may refer to actions or processes of a machine (e.g., a computer with a processing element and other computer hardware components) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or.

The patent claims at the end of this patent application are not intended to be construed under 35 U.S.C. § 112(f) unless traditional means-plus-function language is expressly recited, such as "means for" or "step for" language being explicitly recited in the claim(s).

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

I claim:

1. A computer-implemented method for detecting medical emergency events, the computer-implemented method comprising:
   obtaining, via one or more data sensors, sensor data indicative of kinetic actions of a user, wherein the one or more data sensors comprise one or more accelerometers configured to obtain sensor data comprising acceleration data;

analyzing the sensor data, via one or more processing elements, to associate the sensor data with one or more kinetic actions of the user, wherein the sensor data is analyzed to determine if the user has experienced a kinetic action in the form of a bounce, wherein the kinetic action of the bounce is indicated by the accelerometers measuring a plurality of quick, alternating changes in acceleration;

comparing, via the one or more processing elements, the one or more kinetic actions of the user with a model of kinetic actions to determine whether the one or more kinetic actions correspond with the model of kinetic actions, wherein the model of kinetic actions is indicative of a medical emergency event; and upon determining that the one or more kinetic actions correspond with the model of kinetic actions, contacting, via one or more transceivers, medical emergency responders to request medical emergency services for the user.

2. The computer-implemented method of claim 1, wherein the sensor data comprises orientation data.

3. The computer-implemented method of claim 1, wherein the sensor data comprises geolocation data.

4. The computer-implemented method of claim 1, wherein the data sensors are further selected from one or more of the following: magnetometers, gyroscopes, global positioning system elements, and barometers.

5. The computer-implemented method of claim 1, wherein the one or more processors comprises a processor of a mobile electronic device.

6. The computer-implemented method of claim 5, wherein the mobile electronic device is selected from one of the following: a smartphone, a tablet, a phablet, smart glasses, and a smartwatch.

7. The computer-implemented method of claim 5, wherein the mobile electronic device comprises a smartphone.

8. The computer-implemented method of claim 1, wherein the kinetic actions of the user comprise one or more of the following: the user falling to the ground, the user impacting the ground, and the user remaining motionless.

9. The computer-implemented method of claim 1, wherein the model of kinetic actions comprises a sequential-action model.

10. The computer-implemented method of claim 9, wherein the sequential-action model is representative of a sequence of kinetic actions.

11. The computer-implemented method of claim 10, wherein the sequence of kinetic actions represented by the sequential-action model comprises the following: the user falling to the ground, the user impacting the ground, and the user remaining motionless.

12. The computer-implemented method of claim 11, wherein the kinetic action of falling to the ground represented by the sequential-action model includes falling under an acceleration having a magnitude that corresponds to earth's gravitational acceleration.

13. The computer-implemented method of claim 11, wherein the kinetic action of impacting the ground represented by the sequential-action model includes impacting the ground with a specified impact force.

14. The computer-implemented method of claim 11, wherein the kinetic action of remaining motionless represented by the sequential-action model includes remaining motionless for at least a predetermined period of time.

15. The computer-implemented method of claim 14, wherein the predetermined period of time is 5 seconds.

16. The computer-implemented method of claim 1, wherein the medical emergency event is selected from one or more of the following: a heart attack, a stroke, and a high-velocity impact.

17. The computer-implemented method of claim 9, wherein the one or more kinetic actions of the user correspond with the sequential-action model if the one or more kinetic actions of the user sequentially match the kinetic actions represented by the sequential-action model.

18. A system for detecting medical emergency events, said system comprising:

one or more data sensors configured to obtain sensor data indicative of kinetic actions of a user, wherein the one or more data sensors comprise one or more accelerometers configured to obtain sensor data comprising acceleration data; and a computing device comprising one or more processing elements and one or more transceivers, wherein said computing device is configured to— obtain, from the one or more data sensors, sensor data indicative of kinetic actions of the user, analyze the sensor data, via the one or more processing elements, to associate the sensor data with one or more kinetic actions of the user, wherein the sensor data is analyzed to determine if the user has experienced a kinetic action in the form of a bounce, wherein the kinetic action of the bounce is indicated by the accelerometers measuring a plurality of quick, alternating changes in acceleration, compare, via the one or more processing elements, the one or more kinetic actions of the user with a model of kinetic actions to determine whether the one or more kinetic actions correspond with the model of kinetic actions, wherein the model of kinetic actions is indicative of a medical emergency event, and upon determining that the one or more kinetic actions correspond with the model of kinetic actions, contacting, via the one or more transceivers, medical emergency responders to request medical emergency services for the user.

* * * * *